United States Patent
Wirth et al.

(10) Patent No.: US 8,288,987 B2
(45) Date of Patent: Oct. 16, 2012

(54) DEVICE FOR RECHARGING A BATTERY OF A PORTABLE IONIZING-RADIATION SENSOR

(75) Inventors: Thibaut Wirth, Coublevie (FR); Nicolas Demartinecourt, Voreppe (FR); Robert Neyret, Coublevie (FR)

(73) Assignee: Trixell S.A.S., Moirans (FR)

( * ) Notice: Subject to any disclaimer, the term of this patent is extended or adjusted under 35 U.S.C. 154(b) by 479 days.

(21) Appl. No.: 12/516,558

(22) PCT Filed: Nov. 14, 2007

(86) PCT No.: PCT/EP2007/062309
§ 371 (c)(1),
(2), (4) Date: Aug. 20, 2009

(87) PCT Pub. No.: WO2008/064997
PCT Pub. Date: Jun. 5, 2008

(65) Prior Publication Data
US 2010/0045234 A1    Feb. 25, 2010

(30) Foreign Application Priority Data
Nov. 27, 2006    (FR) ...................................... 06 55133

(51) Int. Cl.
*H02J 7/00* (2006.01)
(52) U.S. Cl. ......................... 320/107; 320/113; 320/115
(58) Field of Classification Search .................. 320/107, 320/113, 114, 115
See application file for complete search history.

(56) References Cited

U.S. PATENT DOCUMENTS

| | | | |
|---|---|---|---|
| 5,221,457 A * | 6/1993 | North et al. .................... | 204/416 |
| 5,828,726 A | 10/1998 | Polichar et al. | |
| 6,438,229 B1 | 8/2002 | Overy et al. | |
| 7,555,363 B2 * | 6/2009 | Augenbraun et al. ........ | 700/253 |
| 2004/0082369 A1 | 4/2004 | Dayan et al. | |
| 2005/0156562 A1* | 7/2005 | Cohen et al. ................... | 320/107 |
| 2006/0034427 A1 | 2/2006 | Brooks | |
| 2006/0108977 A1 | 5/2006 | Kagermeier et al. | |

* cited by examiner

Primary Examiner — M'Baye Diao
(74) Attorney, Agent, or Firm — Stroock & Stroock & Lavan LLP

(57) ABSTRACT

The present invention relates to a device for recharging a battery of a portable ionizing-radiation sensor resting on a recharging base. The sensor includes, on one or more accessible faces, a plurality of electrical-contact areas connected to the battery that powers the sensor. The recharging base comprises a device for mobilizing one or more mobile contacts. The mobile contacts are connected to a power source. The mobile contacts mechanically enter the body (i.e., housing) of the recharging base and mechanically protrude from the body of the recharging base through one or more openings made in the body of the recharging base. The mobile contacts are electrically in contact with the plurality of electrical-contact areas of the sensor if one or more of the plurality of electrical-contact areas are positioned facing the openings when the mobile contacts protrude from the recharging base. An embodiment of the invention may be used for X-ray or Gamma-ray medical imaging.

18 Claims, 3 Drawing Sheets

DEVICE FOR RECHARGING A BATTERY OF A PORTABLE IONIZING-RADIATION SENSOR

CROSS-REFERENCE TO PRIOR APPLICATION

This is a U.S. National Phase Application under 35 U.S.C. §371 of International Application no. PCT/EP2007/062309, filed Nov. 14, 2007, and claims benefit of French Patent Application No. 06 55133, filed Nov. 27, 2006, both of which are incorporated herein. The International Application was published in French on Jun. 5, 2008 as WO 2008/064997 under PCT Article 21 (2).

BACKGROUND OF THE INVENTION

The present invention relates to a device for recharging a battery of a portable ionizing-radiation sensor. The invention is used for example in the field of X-ray or Gamma-ray medical imaging.

BRIEF DESCRIPTION OF THE PRIOR ART

A new type of X-ray sensor, more flexible in its use than the traditional sensors, is used in the field of medical imaging. These are portable X-ray sensors developed for special situations in which conventional equipment cannot easily be used. For example, when a patient cannot be moved, it is necessary to bring the medical radiography equipment to him. Likewise, in the case of certain traumas, it is not always possible to position the patient appropriately in order to orientate that part of the body that is to be radiographed. The use of a portable sensor then allows the radiography equipment to be positioned correctly in order to take a radiographic image of the trauma. Portable sensors therefore allow the image-taking conditions to be tailored to suit the patient rather than the reverse.

Portable sensors may notably be wireless in order to offer better flexibility of use. Wireless sensors require a dedicated recharging station. These charging stations are parts that are accessible to the patient. They therefore meet safety standards relating to accessible parts, such as medical electrical equipment safety standard UL60601-1 for example. These safety standards also cover the electrical contacts of the recharging stations which, in order to avoid any risk of electrocution, must not come into contact with the patient.

The recharging stations have to tolerate a great many charging operations because of the intensity with which medical imaging equipment is used. This use leads to premature wear of the electrical contacts conventionally used. In addition, positioning the sensor on the recharging station is often done by sliding the portable part onto the fixed part, leading to scratching of the sensor and of the electrical contacts of the recharging stations. This scratching notably leads to oxidation of the metal parts which may lead to problems with the quality of the image, associated with shortcomings in the quality of the supply of electrical power. Thus, the various electrical contacts have often to be replaced in order to guard against wearing thereof. This considerably increases the cost of maintaining the sensors and their recharging stations.

The recharging stations currently used do not allow the sensor to be operated while its batteries are being recharged and this, when the sensor is in intensive use, leads to situations in which the sensor can no longer be used because its batteries are not sufficiently charged.

Other recharging solutions involving induction exist and do reduce the risk of damaging and scratching the electrical contacts of the sensor and of the recharging station. However, such recharging stations may generate a significant amount of electromagnetic noise and generate localized heating at the recharging base and these disrupt the sensor during image acquisition. The image may then become locally degraded. This type of recharging station is therefore ill-suited to the recharging of a portable X-ray sensor.

SUMMARY OF THE INVENTION

It is notably one object of the invention to alleviate the aforementioned disadvantages. To this end, a subject of the invention is a device for recharging a battery of a portable ionizing-radiation sensor resting on a recharging base. The sensor includes, on one or more accessible faces, several electrical-contact areas connected to the battery that powers the X-ray sensor. The recharging base includes a device for mobilizing one or more mobile contacts, connected to a power source, which mechanically enter the body (i.e., the housing) of the recharging base and mechanically protrude from the body of the recharging base through one or more openings made in the body of the recharging base, the said mobile contacts being electrically in contact with the contact areas of the sensor if one or more of the contact areas are positioned facing the openings when the said mobile contacts are protruding from the recharging base.

The contact areas are positioned in such a way that they come into contact with the mobile contacts of the recharging base when the accessible face or faces of the sensor are positioned facing the recharging base in one of a number of predefined positions.

The recharging base includes a door, situated on the face of the recharging base that includes the opening or openings, and that adopts two positions: a closed position in which the door closes the opening or openings and an open position in which the door uncovers the opening or openings.

The door, which is mobilized through mechanical dependency on the device that mobilizes the mobile contacts, is in the open position when the mobile contacts are protruding and is in the closed position when the mobile contacts are retracted inside the body of the recharging base.

The contact areas have a polarity that is dependent on their positioning on the accessible face or faces of the sensor, the polarity of the contact areas corresponding to the polarity of the mobile contacts that lie opposite them when the sensor is positioned in one of a number of predefined positions.

The contact areas are fixed to a removable electrical-contact-area plate fixed to the sensor.

The mobile contacts of the recharging base are removable.

Each mobile contact includes a spring.

The sensor is placed on a support to which the recharging base is fixed, the opening or openings in the recharging base facing one or more openings produced in the support.

The device includes a means of cutting off the supply of power to the mobile contacts.

The main advantages of embodiments of the invention are notably that it meets the safety standards that apply to the field of medical imaging while at the same time having flexibility of use that, amongst other things, allows the portable sensor to be used in the standard way.

The device according to embodiments of the invention advantageously makes it possible to limit the wear on the various electrical contacts needed for recharging the battery of the sensor and to make replacement of the electrical contacts easier. All this advantageously makes it possible to reduce the costs of maintaining the recharging device.

BRIEF DESCRIPTION OF THE DRAWINGS

Other features and advantages of the invention will become apparent with the aid of the description which follows, given by way of nonlimiting illustration, with reference to the attached drawings which depict.

DETAILED DESCRIPTION

Figure 1:
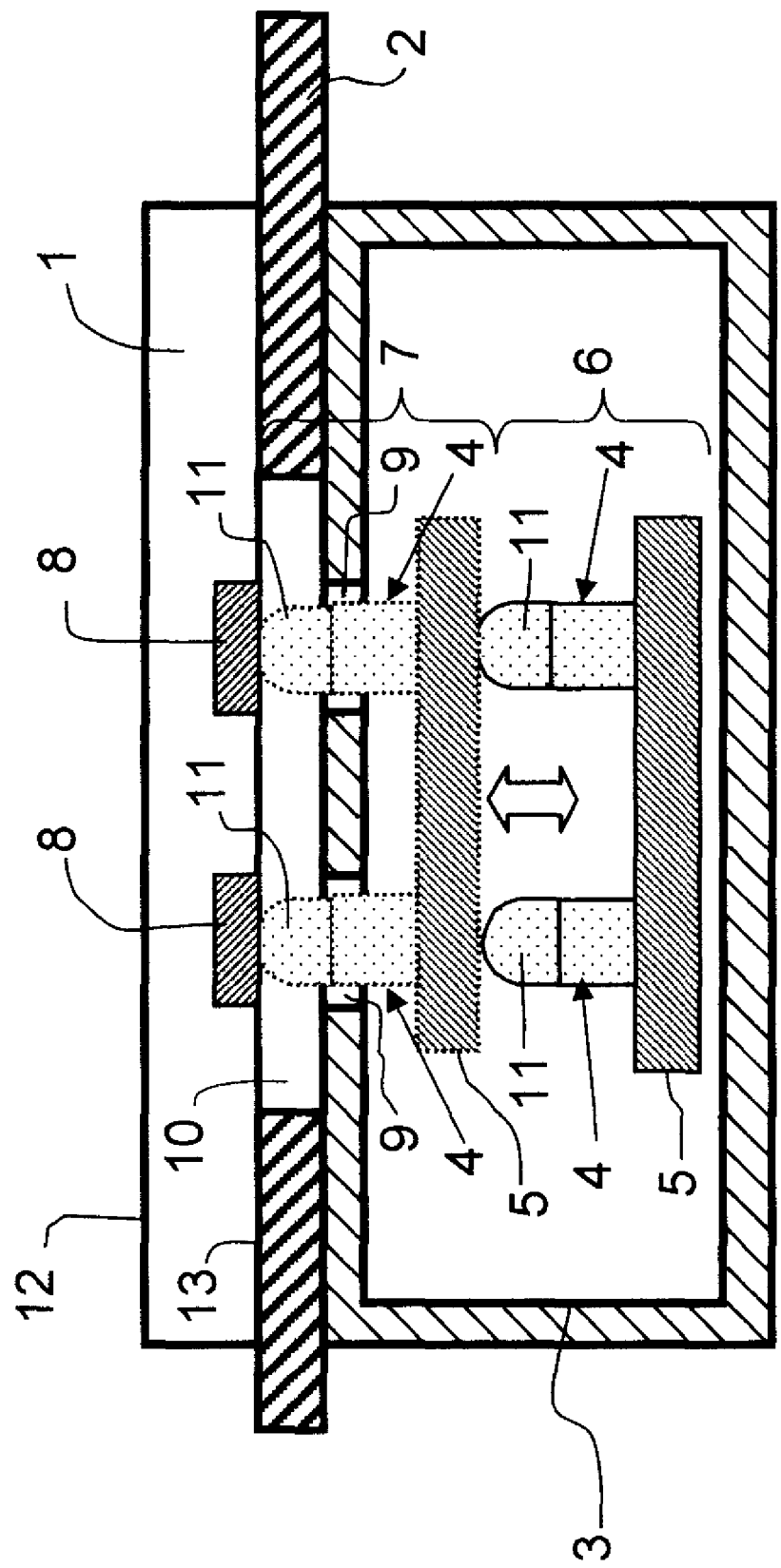
FIG. 1: an operating diagram of the recharging device according to an embodiment of the invention.

FIG. 1 depicts an operating diagram of the recharging device according to an embodiment of the invention. A portable X-ray sensor 1 can be positioned, operated or otherwise, on a support 2. The support 2 may, for example, allow the sensor 1 to be used horizontally in a Bucky table or alternatively allow the sensor 1 to be used vertically in a Bucky stand. The sensor 1 may come in the form of a case comprising at least two faces 12, 13. The first face is a resting face 12 notably comprising an X-ray collection device and which can come into contact with the patient. The second face is an accessible face 13 placed in contact, for example, with the support 2.

A casing 3 comprising a part of the device according to an embodiment of the invention that allows a battery of the sensor 1 to be recharged may be attached under the support 2. This casing 3 is hereinafter termed the recharging base 3. The recharging base 3 may have one or more openings 9 made in the recharging base 3. The openings 9 in the recharging base 3 notably allow one or more mobile electrical contacts 4 to enter or protrude from the recharging base 3.

The mobile contacts 4 may be made in a conducting alloy. They may include a spring allowing them, for example, to maintain mechanical contact with electrical-contact areas 8 of the sensor 1. The mobile contacts 4 may notably include an end in the form of a tip 11 that is rounded in order not to scratch the material with which they come into contact. The second end of each mobile contact 4 is fixed to a plate 5 depicted horizontally in FIG. 1. The mobile contacts 4 may, for example, be screwed to the plate 5 so that they can be easily removed. The mobile contacts 4 are, for example, fixed at right angles to the plate 5. In order to deliver a current needed for charging the battery of the sensor 1, the mobile contacts 4 are electrically powered by an electrical power supply not depicted in FIG. 1 and coupled to a suitable power source.

The plate 5 can be moved vertically between two positions 6, 7. The first position 6 is a position in which the mobile contacts 4 are fully retracted inside the body of the recharging base 3. The first position 6 corresponds to a state in which the sensor 1 is not powered. The second position 7, or protruding position 7, is a position in which the mobile contacts 4 protrude through the opening or openings 9 in the recharging base 3. The mobile contacts 4 pass through the support 2 via one or more openings 10 made in the support 2. The mobile contacts 4 can thus come into contact with the sensor 1. When the mobile contacts 4 are in the protruding position 7, the rounded tip 11 of each mobile contact 4 is in contact with one of the flat contact areas 8 positioned on the accessible face 13 of the sensor 1.

The contact areas 8 are made of an electrically conducting material and are connected to the battery of the sensor 1, which battery is not depicted in FIG. 1.

The use of mobile contacts 4 in the recharging device according to an embodiment of the invention makes it possible to reduce the mechanical contacts of the sensor 1 to those contacts that are strictly necessary for charging the battery of the sensor 1. This then makes it possible to reduce the risk of scratching the contact areas 8 of the sensor 1 and the mobile contacts 4. The life of the various contacts 4, 8 of the sensor 1 and of the recharging base 3 is notably longer by using the recharging device according to an embodiment of the invention.

Figure 2:
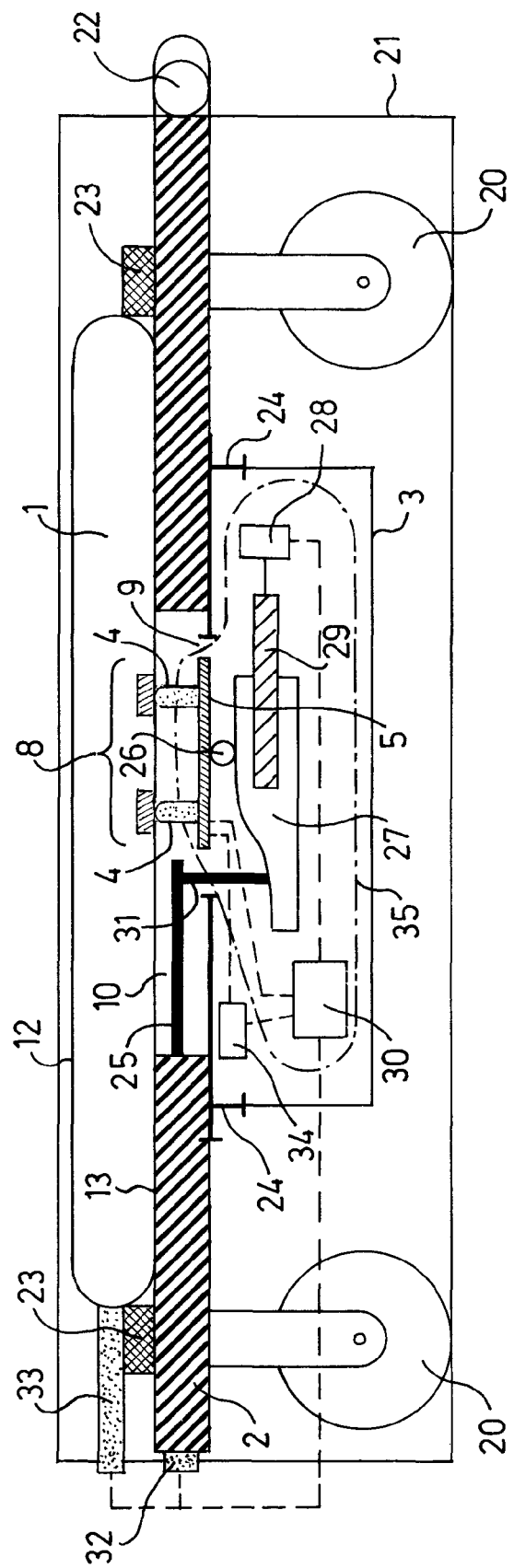
FIG. 2: a simplified diagram of one implementation of the recharging device according to an embodiment of the invention.

FIG. 2 depicts a sectioned view of a horizontal mobile panel which may, for example, be inserted into a Bucky table. The mobile panel is a support 2 which may in particular include wheels 20 allowing the support 2 to enter or leave a casing 21 in a Bucky table. The support 2 may for example be pulled or pushed by a user via a handle 22 situated on one end of the support 2. Extracting the support 2 notably allows the sensor 1 to be placed onto the support 2 or removed from the support 2. The sensor 1 is positioned accurately on the support 2 notably by virtue of chocks 23 which prevent any lateral movement of the sensor 1 on the support 2. The accessible face 13 of the sensor 1 is then in contact with the support 2. The support 2 is notably retracted into the casing 21 when the sensor 1 is being used for radiography, as depicted in FIG. 2.

Fixed under the support 2 is the body of the recharging base 3. Brackets 24, for example screwed, on the one hand, to the body of the recharging base 3, and, on the other hand, to the support 2, hold the recharging base 3 and the support 2 together.

The support 2 has an opening 10 allowing the mobile contacts 4 of the recharging base 3 to come into contact with the contact areas 8 of the sensor 1 when the latter is placed on the support 2.

The recharging base 3 also includes an opening 9 allowing the mobile contacts 4 to protrude from the body of the recharging base 3. The opening 9 in the recharging base 3 can be closed off by a mobile door 25 that opens when the mobile contacts 4 protrude from the recharging base 3 and that closes when the mobile contacts 4 are retracted back into the recharging base 3.

The mobile contacts 4 are fixed, as in FIG. 1, to a plate 5. Fixed to the plate 5 are wheels 26 allowing the plate 5 to move along a mobile ramp 27. The mobile ramp 27 may be set in motion, for example, by a stepping motor 28 driving an endless screw 29 that enters a tapped hole in the mobile ramp 27. The stepping motor 28 may, for example, pull the mobile ramp 27 when it imports a first rotational movement to the endless screw 29. The stepping motor 28 may also push the mobile ramp 27 when the stepping motor 28 imparts a second rotational movement, in the opposite direction to the first rotational movement, to the endless screw 29. The mobile ramp 27 can then move in a horizontal plane. The inclined surface of the mobile ramp 27 allows the plate 5 to move vertically as the mobile ramp 27 moves horizontally.

The horizontal movements of the plate 5 may be prevented, for example, by virtue of the following means, not depicted in FIG. 2: an extension of the axles of the wheels 26 on each side of the wheels 26 may slide in two channels machined in the body of the recharging base for example. These two channels may be perpendicular to the movement of the mobile ramp 27 in order to prevent any horizontal movement of the plate 5 as the mobile ramp 27 is mobilized.

The door 25 may, for example, be driven by the horizontal movement of the mobile ramp 27, notably by being connected to the mobile ramp 27 via a rigid rod 31. The door 25 thus secured to the mobile ramp 27 can close when the mobile ramp 27 is pulled by the stepping motor 28 and can open when the mobile ramp 27 is pushed by the stepping motor 28. When the door 25 is closed, any contact between a foreign body and the mobile contacts 4 can be avoided. This also limits the wearing of the mobile contacts 4 and guarantees safety from an electrical standpoint by preventing any contact between a foreign body and the mobile contacts 4, which may be live.

The stepping motor 28 can be powered by an electrical power supply 30. The electrical power supply 30 may also be connected to the mobile contacts 4 so as to deliver the current needed through recharging the battery of the sensor 1.

The electrical power supply 30, the stepping motor 28, the endless screw 29, the mobile ramp 27, the plate 5 and the wheels 26 form part of one example of a device 35 for mobilizing the mobile contacts 4.

Two push-button devices 32, 33 secured to the casing 21 are able respectively to detect whether the support 2 is present in the casing 21 and whether the sensor 1 is present on the support 2. The push-button 32 is, for example, depressed by the support 2 when the support 2 is pushed into the casing 21. The push-button 33 for example is depressed by the sensor 1 when the latter is positioned on the support 2, the support 2 being pushed into the casing 21. When the push-buttons 32, 33 are depressed, an electrical contact may be made, allowing the electrical power supply 30 to deliver a current to the stepping motor 28 and to the mobile contacts 4. As soon as one of the push-buttons 32, 33 is no longer depressed, the supply of electrical power is cut off. The push-buttons 32, 33 provide the recharging device with twofold safety: any movement of the sensor 1 or of the support 2 automatically cuts off the supply of power to the stepping motor 28 and to the mobile contacts 4.

A circuit breaker device 34 connected, on the one hand, to the electrical power supply 30 and, on the other hand, to the mobile contacts 4, is able to detect short circuits, thus cutting off the supply of power to the stepping motor 28 and to the mobile contacts 4, notably with a view to protecting the latter. This makes it possible for example to guarantee against the risks of electrocution when the recharging device according to an embodiment of the invention is being handled inappropriately.

Figure 3A:
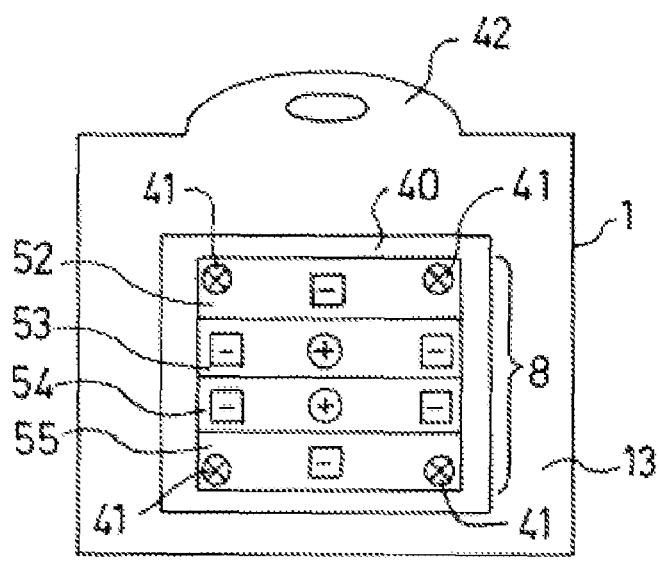
FIG. 3a: a view from above of the X-ray sensor provided with an electrical-contacts plate.
Figure 3B:
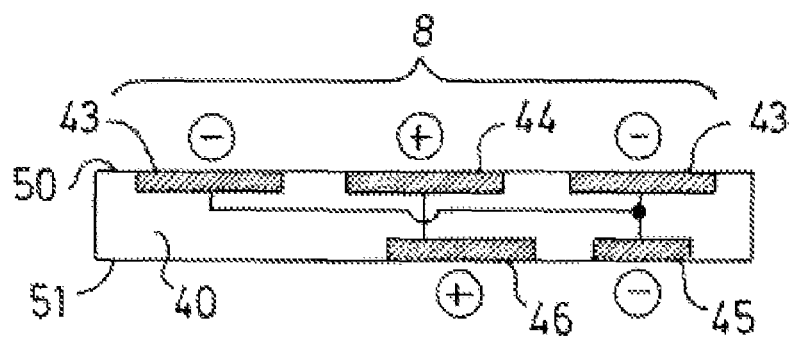
FIG. 3b: a schematic sectioned view of the electrical-contacts plate for the portable X-ray sensor.
Figure 3C:
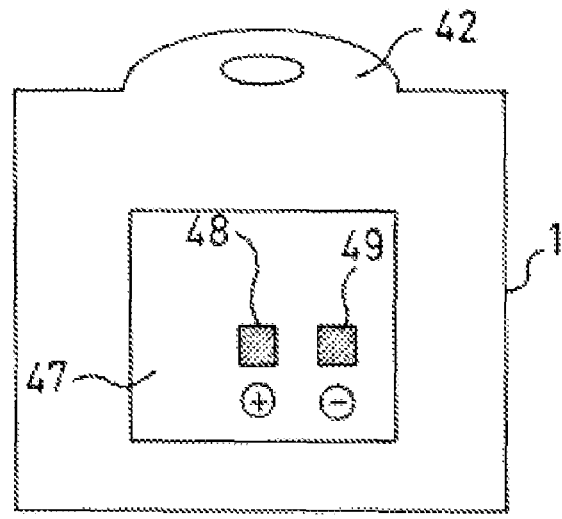
FIG. 3c: a view from above of the portable X-ray sensor without the electrical-contacts plate.

FIGS. 3a, 3b and 3c show an exemplary embodiment of the contact areas 8 positioned on the sensor 1.

FIG. 3a shows a view of the accessible face 13 of the sensor 1 comprising a set of contact areas 8 which are fixed to a contact-area plate 40, for example a rectangular one. The sensor 1 includes, at one of its ends, a handle 42 so that the sensor can be handled with ease. The contact-area plate 40 may notably be screwed to the accessible face 13 of the sensor 1 so as to allow the contact areas 8 to be replaced easily when they are worn. The contact-area plate 40 may be fixed to the sensor 1 by means of four screws 41, for example, each situated at one of the four corners of the contact-area plate 40. The set of contact areas 8 are positioned in such a way that the mobile contacts 4 of the recharging base 3 are in contact with two of the contact areas 8 whatever the position of the sensor 1, when it is placed on the support 2, of the predefined positions that may, for example, be the following positions:

portrait, top: the handle 42 of the sensor 1 being directed towards the top,
portrait, bottom: the handle 42 of the sensor 1 being directed towards the bottom,
landscape, left: the handle 42 of the sensor 1 being directed towards the left,
landscape, right: the handle 42 of the sensor 1 being directed towards the right.

The recharging base 3 may include two mobile contacts 4. A first mobile contact 4 is, for example, positively polarized and a second mobile contact 4 is then negatively polarized. For example, the positively polarized first mobile contact 4 may be situated near the middle of the recharging device. Of the contact areas 8, two may be positively polarized and the others negatively polarized. The contact areas 8 at the positive polarity are, for example, situated in the middle of the contact-area plate 40 and the contact areas 8 of the negative polarity are, for example, situated at the edges of the contact-area plate 40. In one exemplary embodiment, such as in FIG. 3a, eight contact areas 8 may be positioned in four rows 52, 53, 54 and three columns:
the first row 52 may include one contact area 8 in the second column with a negative polarity;
the second row 53 may include three contact areas 8, the contact areas 8 situated in the first and third columns being of negative polarity, the contact area 8 in the second column being of positive polarity;
the third row 54 may include three contact areas 8 of the same polarity positioned in the same way as the three contact areas 8 of the second row 53;
the fourth row 55 may include one contact area 8 of negative polarity, positioned in exactly the same way as the contact area of the first row 52.

An arrangement such as this allows the sensor 1 to be positioned on the support 2 in one of the aforementioned positions. This also makes it possible to avoid any short circuiting if the sensor is incorrectly positioned on the support 2, all possible positions of the sensor 1 on the support 2 being catered for.

FIG. 3b shows a schematic sectioned view of the contact-area plate 40. The contact-area plate 40 includes an outer first face 50, notably continuous with the accessible face 13 of the sensor 1 when the contact-area plate 40 is screwed to the sensor 1. The contact-area plate 40 includes a second face 51 internal to the sensor 1 when the contact-area plate 40 is screwed onto the sensor 1. FIG. 3b notably depicts three of the contact areas 8. These three contact areas 8 are therefore positioned on the exterior face 50 of the contact-area plate 40. Of the three contact areas 8, two lateral contact areas 43 are, for example, negatively polarized and one central contact area 44 is, for example, positively polarized. The two lateral contact areas 43 are electrically connected to a first interior contact area 45 situated on the interior second face 51 and negatively polarized. Likewise, the interior contact area 44 is connected to an interior second contact area 46 situated on the interior second face 51 and positively polarized.

FIG. 3c depicts the accessible face 13 of the sensor 1 without the contact-area plate 40. The sensor 1 therefore includes a rectangular cavity 47 able to accommodate the contact-area plate 40. In the bottom of this cavity 47 there are two contacts 48, 49. The first contact 49 may, for example, be negatively polarized and positioned in such a way as to come into contact with the interior first contact area 45 situated on the interior face 51 of the contact-area plate 40 when the contact-area plate 40 is positioned in the cavity 47 and fixed to the sensor 1. Likewise, the second contact 48 may, for example, be positively polarized and positioned in such a way as to come into contact with the interior second contact area 46 when the contact-area plate 40 is positioned in the cavity 47 and fixed to the sensor 1. The contacts 48, 49 are electrically connected to a battery of the sensor 1, which battery is not depicted in FIG. 3c.

The contact-area plate 40 can therefore easily be replaced on the sensor 1; all that is required is for it to be removed when the contact areas 8 have become worn, and replaced with a new contact-area plate.

In another embodiment of the device according to the invention, the support 2 may form part of the recharging base 3.

In another embodiment of the device according to the invention, the contact areas 8 of the sensor 1 may be on one or more sides of the sensor 1. The accessible face 13 may then include several sides of the sensor 1.

The invention may notably be applied to any wireless equipment that has to be recharged on a base in different positions, where there is a high risk that the contact zones will become scratched.

Positioning the charging base 3 in a Bucky table or a Bucky stand advantageously allows the sensor 1 to be used in the same configurations as conventional sensors.

Another advantage of the device according to an embodiment of the invention is that it allows the portable sensor 1 to adopt different positions on the support 2, making the portable sensor 1 very flexible in its use.

Advantageously, the recharging device according to an embodiment of the invention allows the sensor 1 to be recharged while it is in use: indeed using electrical contacts as a source for powering a battery of the sensor 1 allows the sensor 1 optimal operation because electromagnetic emissions are then very low. There is therefore no risk of the image being contaminated when the sensor 1 is being recharged while it is in operation.

The recharging device according to an embodiment of the invention advantageously meets the safety standards in force in the medical environment, such as, for example, standard IEC60601-1 or UL60601-1 relating notably to the resting parts such as the resting face 12 of the sensor 1 and the electrical safety of the recharging base 3 by way of an accessible part.

Wear of the mobile contacts 4 of the recharging base 3 is advantageously limited by virtue of the facts that the mobile contacts 4:
- are positioned inside the body of the recharging base 3 when not in use;
- can be made to protrude only when the sensor 1 is correctly positioned on the support 2 with a view to being recharged.

The set of contacts of the recharging device comprising the mobile contacts 4 of the recharging base 3 and the contact areas 8 of the sensor 1 has the advantage that it can easily be removed to facilitate maintenance of the recharging device. This ease of maintenance advantageously guarantees that the contacts will always be in good condition, making it possible for example to have scratch-free contacts which therefore comply with the safety and quality regulations relating to the field of medicine.

The ease with which the contacts can be removed advantageously makes it possible to reduce the costs of maintaining the recharging device according to an embodiment of the invention.

The invention claimed is:

1. A device for recharging a battery of a battery-powered portable ionizing-radiation sensor having a sensor and a recharging base to recharge the sensor, the sensor configured to rest on the recharging base, wherein:
   the sensor comprises:
      one or more accessible faces;
      a plurality of electrical-contact areas on the one or more accessible faces, the plurality of electrical-contact areas electrically connected to the battery that powers the sensor; and
   the recharging base comprises:
      a housing having one or more openings; and
      one or more mobile contacts electrically connected to a power source, the one or more mobile contacts movable between a first position and a second position, wherein when in the first position the one or more mobile contacts protrude from the housing through at least one of the one or more openings in the housing, and when in the second position the one or more mobile contacts are retracted inside the housing, and wherein the one or more mobile contacts are configured to electrically contact at least a portion of the plurality of electrical-contact areas of the sensor if one or more of the plurality of electrical-contact areas are positioned facing the one or more openings of the housing when the mobile contacts are in the first position protruding from the recharging base.

2. The device according to claim 1, wherein the plurality of electrical-contact areas contact the mobile contacts of the recharging base when the one or more accessible faces of the sensor are positioned facing the recharging base in one or more predefined positions.

3. The device according to claim 1, wherein the recharging base comprises a door, the door configurable into a closed position that closes the one or more openings, and the door further configurable into an open position that uncovers the one or more openings, wherein the one or more mobile contacts are in the first position when the door is in the open position, and the one or more mobile contacts are in the second position when the door is on the closed position.

4. The device according to claim 3, further comprising a mechanism that moves both the door and the one or more mobile contacts.

5. The device according to claim 1, wherein each electrical-contact area is configured to have a polarity that is dependent on a position of the electrical-contact area on the one or more accessible faces of the sensor, the polarity of each electrical-contact area corresponding to a polarity of a mobile contact that lies opposite said electrical-contact area when the sensor is positioned in a predetermined position.

6. The device according to claim 1, wherein the plurality of electrical-contact areas are affixed to a removable electrical-contact-area plate, and the removable electrical-contact-area plate is affixed to the sensor.

7. The device according to claim 1, wherein at least one of said one or more mobile contacts of the recharging base is removable.

8. The device according to claim 1, wherein at least one of said one or more mobile contacts comprises a spring.

9. The device according to claim 1, wherein the sensor is configured to be positionable on a support to which the recharging base is affixed, the one or more openings in the recharging base facing one or more openings in the support.

10. The device according to claim 1, further comprising a switch for selectively applying power to the mobile contacts.

11. A recharging base for recharging a battery of a portable device when the portable device is resting on the recharging base, wherein the recharging base comprises:
   a housing having one or more openings; and one or more mobile contacts electrically connected to a power source, the one or more mobile contacts movable between a first position and a second position, wherein when in the first position the one or more mobile contacts protrude from the housing through at least one of the one or more openings in the housing, and when in the second position the one or more mobile contacts are retracted inside the housing, and wherein the one or more mobile contacts are configured to electrically contact at least a portion of a plurality of electrical-contact areas of the portable device if one or more of the plurality of electrical-contact areas are positioned facing the one or more openings of the housing when the mobile contacts are in the first position protruding from the recharging base.

12. The device according to claim 11, wherein a plurality of electrical-contact areas of the portable device contact the mobile contacts of the recharging base when the plurality of electrical-contact areas of the portable device face the recharging base in one or more predefined positions.

13. The device according to claim 11, wherein the recharging base comprises a door, the door configurable into a closed position that closes the one or more openings, and the door further configurable into an open position that uncovers the one or more openings, wherein the one or more mobile contacts are in the first position when the door is in the open position, and the one or more mobile contacts are in the second position when the door is on the closed position.

14. The device according to claim 13, further comprising a configured to move both the door and the one or more mobile contacts.

15. The device according to claim 11, wherein at least one of said one or more mobile contacts of the recharging base is removable.

16. The device according to claim 11, wherein at least one of said one or more mobile contacts comprises a spring.

17. The device according to claim 11, further comprising a support to which the recharging base is affixed, the one or more openings in the recharging base facing one or more openings in the support, wherein the portable device is is configured to be positionable on the support.

18. The device according to claim 11, further comprising a switch for selectively applying power to the mobile contacts.

* * * * *